US005741959A

United States Patent [19]
Garcia, Jr. et al.

[11] Patent Number: 5,741,959
[45] Date of Patent: Apr. 21, 1998

[54] PORTABLE TESTER FOR DETERMINING GAS CONTENT WITHIN A CORE SAMPLE

[75] Inventors: Fred Garcia, Jr., Donora; Steven J. Schatzel, Bethel Park, both of Pa.

[73] Assignee: The United States of America as represented by the United States Department of Energy, Washington, D.C.

[21] Appl. No.: 694,574

[22] Filed: Aug. 9, 1996

[51] Int. Cl.[6] ................................................. G01N 7/00
[52] U.S. Cl. .................................. 73/19.05; 73/152.11
[58] Field of Search ...................... 73/38, 190.5, 23.2, 73/431, 19.01, 152.11; 422/92

[56] References Cited

U.S. PATENT DOCUMENTS

| | | | |
|---|---|---|---|
| 3,135,108 | 6/1964 | Santeler | 73/23.2 |
| 4,830,579 | 5/1989 | Cheng | 73/431 X |
| 4,870,863 | 10/1989 | Duncan et al. | 73/431 |
| 4,920,799 | 5/1990 | Low | 73/431 |
| 5,261,267 | 11/1993 | Kamath et al. | 73/38 |
| 5,265,462 | 11/1993 | Blauch et al. | 73/38 |
| 5,299,140 | 3/1994 | Ankeny et al. | 73/38 X |
| 5,311,766 | 5/1994 | Persoff et al. | 73/38 |
| 5,342,580 | 8/1994 | Brenner | 422/92 |
| 5,436,165 | 7/1995 | Brenner | 436/149 |
| 5,581,033 | 12/1996 | Hess | 73/431 |

OTHER PUBLICATIONS

Bureau of Mines Report of Investigation 9063 (1987) 31 pages.
The Modified Direct Method of Gas Content Determination: Application and Results Ulery, et al., 11 pages May 1991.

*Primary Examiner*—Hezron E. Williams
*Assistant Examiner*—Jay L. Politzer
*Attorney, Agent, or Firm*—Mark LaMarre; Mark P. Dvorscak; William R. Moser

[57] ABSTRACT

A portable tester is provided for reading and displaying the pressure of a gas released from a rock core sample stored within a sealed container and for taking a sample of the released pressurized gas for chemical analysis thereof for subsequent use in a modified direct method test which determines the volume of gas and specific type of gas contained within the core sample. The portable tester includes a pair of low and high range electrical pressure transducers for detecting a gas pressure; a pair of low and high range display units for displaying the pressure of the detected gas- a selector valve connected to the low and high range pressure transducers, a selector knob for selecting gas flow to one of the flow paths; control valve having an inlet connection to the sealed container, and outlets connected to: a sample gas canister, a second outlet port connected to the selector valve means for reading the pressure of the gas from the sealed container to either the low range or high range pressure transducers, and a connection for venting gas contained within the sealed container to the atmosphere. A battery is electrically connected to and supplies the power for operating the unit. The pressure transducers, display units, selector and control valve means and the battery is mounted to and housed within a protective casing for portable transport and use.

6 Claims, 3 Drawing Sheets

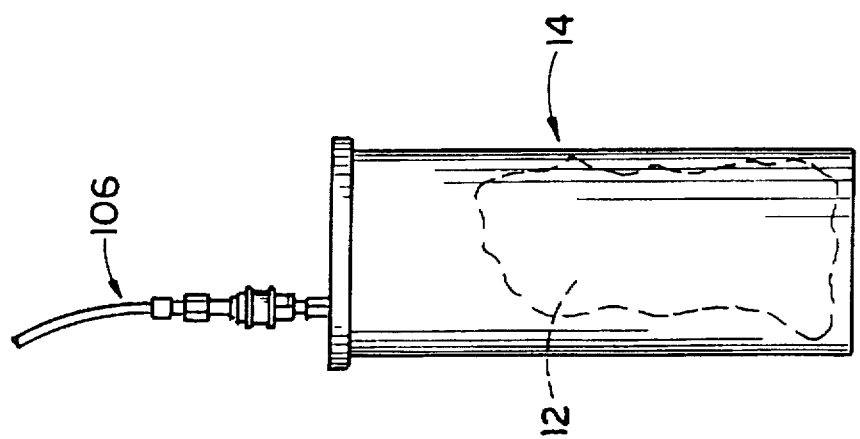
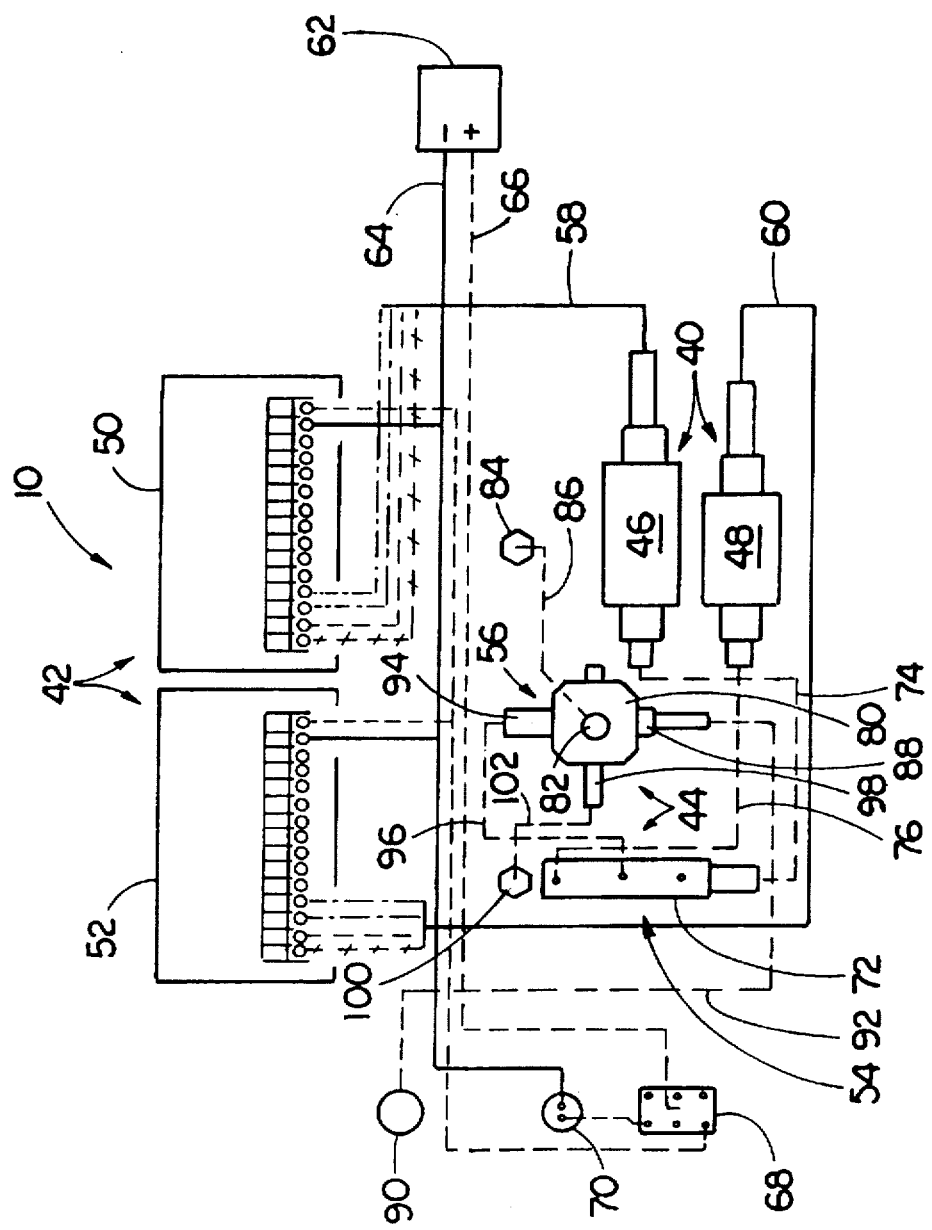

PORTABLE TESTER FOR DETERMINING GAS CONTENT WITHIN A CORE SAMPLE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention relates generally to a tester for use in determining the content of a gas within a core sample which is useful in various mining operations, such as coal mining.

2. Description of the Prior Art

In the formation of coal, various gases are formed. Methane is one of these gases and is the major gas component of most underground coal reserves. The need for a test to measure the amount of methane in coal was recognized by the coal mining industry so that adequate ventilation could be planned for underground miners to avoid ignition and explosion hazards associated with methane concentrations between 5 and 15 percent in air. Also, since the 1970's, there has been considerable interest in coalbed gas as an energy source and the coalbed methane industry requires a variety of reservoir information for decision making prior to drilling expensive production boreholes. One of the most fundamental pieces of information for the selection of production sites is methane content data.

The existing technology for conducting methane content testing of coal begins by retrieving a coal sample and then placing the sample in an airtight container. As the coal sample sets within the airtight container, gas within the micropores of the coal is released. One end of a small diameter flexible tube is joined to the airtight container and the other end is connected to a calibrated vessel containing a column of water with an attached reservoir. When a valve on the airtight container is opened, the accumulated gas released from the coal flows through the tubing and displaces a portion of the column of water equal to the coal gas volume. This procedure is repeated periodically to determine the total gas content of each coal sample at the sample site. Total gas content is the sum of all the gas volume readings for an individual sample and is usually reported as the gas volume divided by the sample mass. Although the variety of existing methane content tests differ in equipment and procedures, these characteristics are generally common to all of them.

The similarities among current methane content testing equipment produce a set of common limitations for these instruments. Some of the problems encountered is due to the use of water in the measurement of gas volume. The water columns and reservoirs can be difficult to handle, assemble, fill, and operate in often rugged terrain where underground boreholes or surface exploratory are drilled. Also, in cold temperatures, the water can be subject to freezing. Another problem with the measurement of coalbed gas by water displacement is the movement of water soluble gases. Methane has a very limited ability to dissolve in water at typical atmospheric pressures. Other chemicals contained in the coalbed gas, such as carbon dioxide, have much higher solubilities and can escape measurement as they dissolve in the water. Still, another problem related to the use of water displacement methods is their low sensitivity to coal samples with relatively little gas content. Tests have shown that the water column may not measure gas present at pressures below about 5 inches water gauge. Problems with excessive head space (the amount of volume in a sample container which is not occupied by the coal sample) have also been found with the current methane content determination technology. When the head space is too large, the accuracy of many current methane tests drops off due to the limited sensitivity of the instrumentation. Errors of up to 30 percent of actual methane contents have been documented.

Other problems with the current methane content measurement technologies are related to the lack of a well defined chemical analysis of coalbed gas altogether. Although methane generally makes up over 90 percent of the coalbed gas in the United States, examples of carbon dioxide and higher hydrocarbons making up unusually large fractions of coalbed methane are known to occur. Assuming all coalbed gas to be methane can lead to erroneous conclusions regarding the estimated methane in place. Determining the chemical composition of only a couple of gas samples over the entire monitoring life of a coal sample can produce misleading results because different gases can be liberated by the coal at variable rates over time since sample monitoring generally requires months to complete. The behavior of oxygen in sample containers demonstrates the importance of chemical analyses of gas samples. Starting with about 21 percent oxygen, some of the oxygen reacts with the coal sample decreasing the volume of oxygen in the container. This loss of oxygen generally levels off after a few days but the result is that part of the gas liberation (volume increase) from the coal sample has been masked by the reactivity of oxygen (volume decrease). Measuring the total gas produced by a sample without chemical analysis will underestimate the methane content of the sample because the loss of oxygen has subtracted from the net change in gas volume.

In the late 1980's, the US Bureau of Mines developed a nondestructive testing methodology, referred to as the Modified Direct Method (MDM) test for determining the gas content of rock and coal samples. The MDM test procedure is well known in the industry, being published in the Bureau of Mines Report of Investigation 9063 in 1987. Briefly, the MDM test uses the ideal gas law to relate differential gas pressure to gas volume at a set of standard temperature and pressure (STP) conditions and its procedural steps begin with the removal of a mineral sample, such as coal or rock, from a site and inserting it into an airtight container for gas content monitoring. The time, barometric pressure and ambient temperature are recorded at the beginning of monitoring and at each monitoring point in time. During each monitoring period, the operator records atmospheric pressure, ambient temperature, differential pressure of the container atmosphere (relative to atmospheric pressure), retrieves a sample of gas from the container, bleeds the container atmosphere to decrease the differential pressure to slightly greater than atmospheric, and records the final container pressure. Bleeding the accumulated gas from the container avoids gas pressure buildup so that conditions for gas release from the mineral sample is relatively constant over the monitoring period. The concentrations of a predetermined set of individual gas species is resolved by performing gas chromatography on the bottled samples. At the beginning of the test procedure, the free space volume of the container with the sample is estimated from the inside dimensions of the container and the outside dimensions of the sample. Knowing the gas pressure, temperature, free space and gas composition, the STP volume of each gas constituent can be determined at any monitoring interval. The difference between the gas contained at the end of one monitoring period (after bleeding the container) to the gas in the container at the start of the next monitoring point (before bleeding the container) is due to the gas liberated from the sample and the addition or loss of gases due to chemical reactions, if they occur. The actual volume of a gas species released from the sample between two monitoring intervals can be determined by calculating the difference between the volume of gas in the container after bleeding the gas and the gas volume in the container at the subsequent monitoring point when the differential pressure is first determined. Summing the gas volume differences over the entire monitoring interval gives the gas content of a particular gas species. These gas volumes are usually normalized for the sample mass. Final free space determinations are made by determining the volume of water required to fill the free space in the container containing the sample. All gas data is then recalculated using this corrected free space data.

Following the initial development of the MDM test and the wide spread interests in this technology, the testing apparatus underwent cycles of modification, evaluation, refinements, and constant revisions to design a testing apparatus to overcome the shortcomings of the prior art testers and one having reduced size and weight, improved packaging, durability and performance to meet the needs and requests of other government agencies, coalbed methane producers, researchers and consultants.

SUMMARY OF THE INVENTION

The present invention provides a portable tester designed to satisfy the aforementioned needs. The portable tester of the present invention is small in size, light in weight, rugged in construction, self-contained and portable so it can be easily transported to and operated in various adverse environmental conditions such as experienced in many mining operations. The low cost portable tester is designed to be user friendly and be operated in the lab by just one person and requires no more than two people for operation in the field. Durability problems associated with tests utilizing extensive glassware have been substantially eliminated through the use of electronic instruments and packaging. The use of electronic pressure transducers instead of water displacement not only eliminates errors produced by water soluble gases and minimizes the potential negative impact of head space on the test results but also eliminates the mess associated with and the problems of freezing conditions when using water. Gas compositional analysis by gas chromatography on samples retrieved from the portable tester alleviates the inaccuracy problem caused by depletions in oxygen. Gas chromatographic analysis also alleviates problems associated with incorrect assumptions regarding the chemical composition of coalbed gas. By incorporating pressure transducers into the portable tester, differential pressure readings can be obtained with a minimal volume of gas loss. The transducers offer superior resolution compared to any other instrumentation incorporated in any existing methane content testing apparatus. And digital readouts enhance the accuracy of the tester by removing the possibility of rounding errors. Additionally, the high resolution, high sensitivity instruments incorporated in the portable tester enhances the ability of the MDM test to determine gas contents of non-coal rock. This is a significant advance in three applications. Some coal mining techniques produce the most gas from rock beds adjacent to the mined coalbed which makes estimating the gas present in these rock units very important in the design of ventilation systems. The second application is in estimating gas contents in non-coal mines, since the flow of gas in these type mines also pose a hazard to underground workers. And the third application for the portable tester of the present invention is in the coalbed methane industry which utilizes the gas content measurement of coal and non-coal rock units and evaluates them for gas production potential.

Accordingly, the present invention is directed to a portable tester for reading and displaying the pressure of a gas released from a rock core sample, such as coal or other minerals, stored within a sealed container and for taking a sample of the released pressurized gas for chemical analysis thereof for subsequent use in a modified direct method test which determines the volume of gas and specific type of gas contained within the core sample. The tester is a self-contained unit with its various components being housed with a protective casing including a box-like hollow base, a mounting plate extending over the box-like base, and a hinged enclosure cover. The various components of the tester are mounted on the undersurface of the plate and disposed between the plate and a bottom wall of the base so as to protect these components from rough handling and the dirty environments, while the control knobs for operating these components and the visual displays are positioned on the top surface of the plate for easy viewing and operability by the operator once he unlatches and opens the hinged cover.

The portable tester further comprises: (a) detector means for detecting a gas pressure and for producing a signal related to the detected pressure; (b) display unit means operably connected to the detector means for receiving a signal produced therefrom and displaying the pressure of the detected gas; (c) valve means having an inlet port for flow communication to the sealed container, a first outlet port for flow communication to a sample gas canister, a second outlet port in flow communication with the detector means for reading the pressure of the flow of gas from the sealed container to the detector means, and a control knob for selecting the flow of gas from the inlet port to one of the first and second outlet ports; and (d) a power source electrically interconnecting the detector means with the display unit means.

More particularly, the detector means includes a low range electrical pressure transducer for detecting a gas pressure within a first range and for producing an electrical signal related to the detected pressure, and a high range electrical pressure transducer for detecting a gas pressure within a second range and for producing an electrical signal related to the detected pressure, with the second range of gas pressure being greater than the first range of gas pressure. Preferably, the first range of gas pressure is between 0–25 pounds per square inch absolute and the second range of gas pressure is between 0–200 pounds per square inch gauge.

In the preferred embodiment, the display unit means includes a low range display unit electrically connected to the low range electrical pressure transducer for receiving the electrical signal produced therefrom and visually displaying the pressure of the detected gas, and a high range display unit electrically connected to the high range electrical pressure transducer for receiving the electrical signal produced therefrom and visually displaying the pressure of the detected gas. In the exemplary form shown, the display units are digital display units operable to display the detected gas pressure in digital numeric units.

And further, in the preferred embodiment, the valve means includes selector valve means in flow communication with the low range and high range pressure transducers and having a first flow path to the low range pressure transducer and a second flow path to the high range pressure transducer and a selector knob for selecting gas flow to either the first flow path or the second flow path. The valve means further includes control valve means having an inlet port for flow communication to the sealed container, a first outlet port for flow communication to a sample gas canister, a second outlet port in flow communication with the selector valve means for reading the pressure of the flow of gas from the sealed container to the first and second flow paths of the respective low range and high range pressure transducers, and a control knob for selecting the flow of gas from the inlet port to one of the first and second outlet ports. The control valve means further includes a third outlet port for venting to the atmosphere gas contained within the sealed container, the control knob being movable for selecting the flow and nonflow of gas from the inlet port to one of the first, second and third outlet ports.

Additionally, the portable tester further comprises a power source in the form of a battery electrically interconnecting the low and high range pressure transducers with the respective low and high range digital display units. Also a switch as been incorporated in the tester for electrically turning on and off the supply of power from the battery to the display units and transducers and a charging connector has been added for recharging of the battery when it becomes low in power. The switch and charging connector are also mounted on the top surface of the mounting plate along with the control knobs for easy access by the operator.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which:

FIG. 4 is a diagrammatic representation of the components of the tester showing the electrical connections and the pneumatic flow paths between the components.

FIG. 5 is an illustrative example of a sealed container for storing of the sample which produces the released gas measured by the tester.

DETAILED DESCRIPTION OF THE INVENTION

Figure 1:
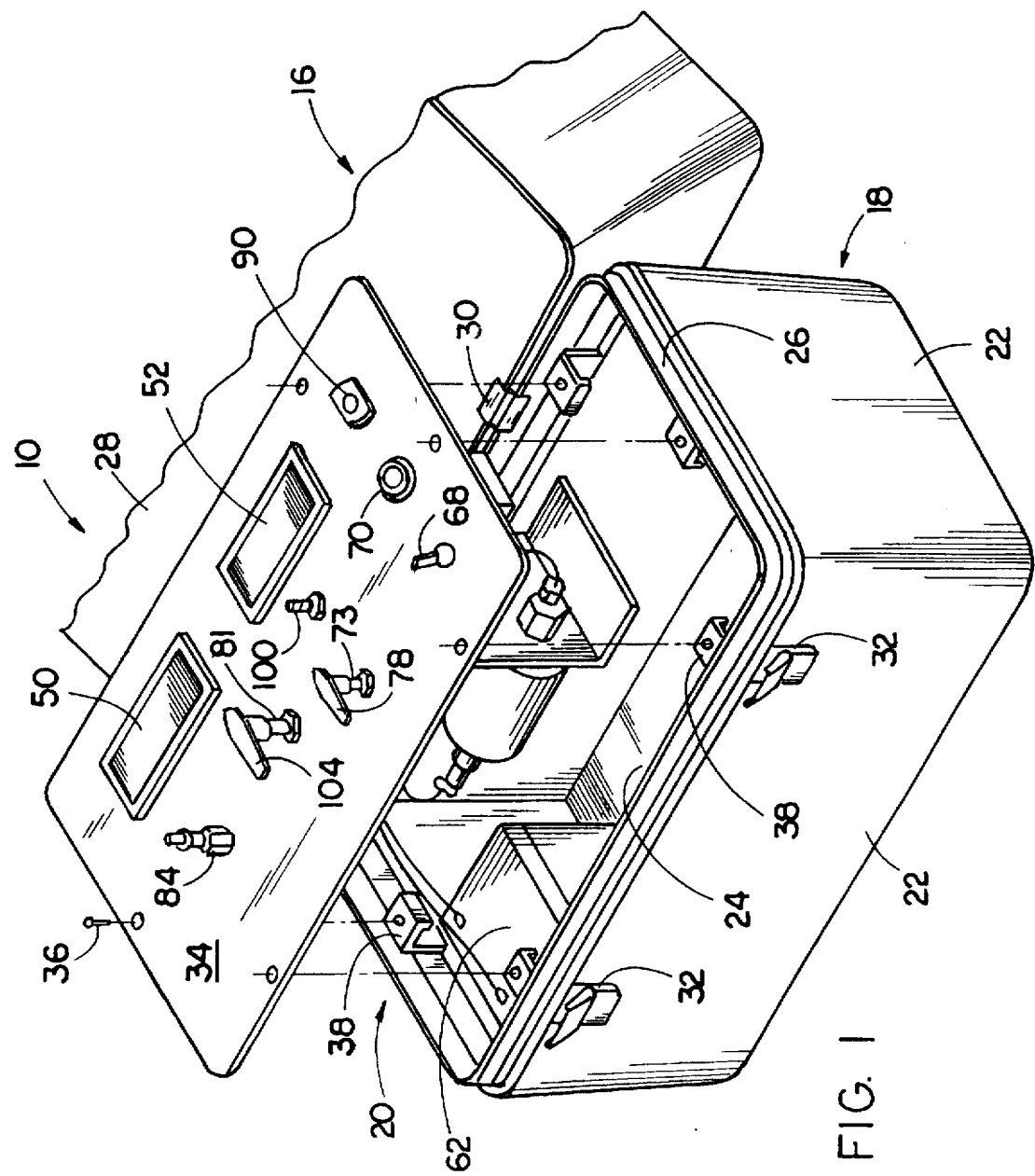
FIG. 1 is an exploded perspective view of the portable tester constructed in accordance with the principles of the present invention.

In the following description, like reference characters designate like or corresponding parts throughout the several views. Also in the following description, it is to be understood that such terms as "forward", "rearward", "left", "right", "upwardly", "downwardly", and the like, are words of convenience and are not to be construed as limiting terms.

Referring now to the drawings, and particularly to FIG. 1 and also FIG. 5, there is shown a portable tester, generally indicated by the numeral 10, being constructed in accordance with the principles of the present invention. The tester 10 is able to read and display the pressure of a gas released from a rock core sample 12, illustrated in FIG. 5, stored within a sealed container 14 and for taking a sample of the released pressurized gas for chemical analysis thereof for subsequent use in a modified direct method test which determines the volume of gas and specific type of gas contained within the core sample 12. The tester 10 has been designed to be a small, light weight, portable self-contained unit so that it can be easily transported by one individual to various field sites. As such, the various components of the portable tester 10 are housed within a protective casing 16 to protect the components from abusive use and to keep dirt and moisture away from the components. The protective casing 16 is a purchased item, being of metal or appropriate synthetic material, and includes a hollow, rectangular box-like base 18 having a top opening 20 and being formed by upstanding sidewalls 22 and a bottom-wall 24. The upper peripheral edge of the sidewalls 22 are offset to form a rim 26 for receiving the lower peripheral edge of a mating enclosure cover 28. The cover 28 is swingably connected to the base 18 by a pair of hinges 30 (only one being seen in FIG. 1) attached to and extending along the rear sidewall of the cover 28 and the corresponding rear sidewall of the base 18 so that the cover can be easily opened and closed on the base 18. A pair of latches 32 on the front sidewall 22 of the base 18 cooperate with latch members (not shown) on the front sidewall of the cover 28 for securing the cover in its closed position. Extending across the top opening 20 of the base 18 is a mounting plate 34 which is suitably attached to the base 18 by screws 36 that are received by mounting brackets 38 affixed on the upper ends of the base sidewalls 22.

Now referring to FIGS. 1–4 and particularly FIG. 4, the components of the portable tester 10 which are housed within the protective casing 16 will be described. The tester 10 basically includes detector means 40 for detecting a gas pressure released from the core sample 12 stored within the sealed container 14, display means 42 for displaying the detected gas pressure, and valve means 44 for communicating the flow of gas released from the sealed container 14 to the detector means 40. In the preferred embodiment, the detector means 40 takes the form of a pair of electrical pressure transducers 46, 48; the display means 42 takes the form of a pair of corresponding digital display units 50, 52; and the valve means 44 takes the form of a pair of valve assemblies and associated flow conduits, namely selector valve means 54 and control valve means 56.

The pair of pressure transducers 46, 48 includes a low range electrical pressure transducer 46 which operates to produce an electric signal related to the detected pressure within a range of pressure between 0–25 pounds per square inch absolute (psia) and a high range electrical pressure transducer 48 which operates to produce an electric signal within a range of pressure between 0–200 pounds per square inch gauge (psig). For visually displaying the pressure detected, the low pressure transducer 46 is electrically connected via wire lead 58 to the corresponding low range display unit 50 and the high range pressure transducer 48 is electrically connected via wire lead 60 to the corresponding high range display unit 52. Preferably, the display units 50, 52 are digital display units operable to display the detected gas pressure in digital numeric units which enhances the accuracy of the tester 10 by removing the possibility of rounding errors.

For operation of the pressure transducers 46, 48 and corresponding display units 50, 52, a source of power, such as a rechargeable battery 62, is provided which is electrically connected to the transducers 46, 48 via the wire leads 64, 66. The supply of electric power from the battery 62 to the transducers 46, 48 and display units 50, 52 is controlled by a conventional on-off switch 68 interconnected in battery lead 66, and for convenient recharging of the battery 62, a recharging connector 70 is electrically interconnected between the battery leads 64, 66.

The selector valve means 44 is in flow communication with the low range and high range pressure transducers 46, 48 and includes a selector valve 72 with a first flow path conduit 74 connected to the low range pressure transducer 46 and with a second flow path conduit 76 connected to the high range pressure transducer 48. The inclusion of two pressure transducers of different pressure ranges minimizes the amount of error associated with each monitoring point by allowing a choice of transducers so that they can be operated within their optional range, that is, the first (low) pressure transducer 46 having a preferred operating range of from 0–25 psia whereas the second (high) pressure transducer 48 having a preferred operating range of from 0–200 psig. A selector knob 78 is provided on the selector valve 72 whereby an operator can move the valve between a first low flow position permitting the gas, via conduit 74, to flow to the low pressure transducer 46 and a second high flow position permitting the gas, via conduit 76, to flow to the high pressure transducer 48.

The control valve means 56 includes a control valve 80 with an inlet port 82 connected to inlet orifice 84, via conduit 86, for flow communication to the sealed container 14, a first outlet port 88 connected to sample orifice 90, via conduit 92, for flow communication to a sample gas canister or vacutainer bottle (not shown), a second outlet port 94 in flow communication, via conduit 96, with the selector valve 72 for reading the pressure of the flow of gas from the sealed container 14 (containing sample 12) to the first and second flow paths 74, 76 of the respective low and high range pressure transducers 46, 48, and preferably, a third outlet port 98 connected to a bleed orifice 100, via flow conduit 102, for venting to the atmosphere gas contained within the sealed container 14. A control knob 104 is provided on control valve 80 for an operator to move the valve 80 from a nonflow "off" position to one of three flow positions. The first flow position, being referred to as the "sample" position, connects the inlet port 82 to the first outlet port 88 whereby the pressurized gas flows from the sealed container 14, via a quick connect-disconnect tubing conduit 106, to and through the control valve 80 (via inlet orifice 84 and conduit 86) and out through the sample orifice 90 via conduit 92 to the gas sample canister (not shown). The second flow position, being referred to as the "read" position, connects the inlet port 82 to the second outlet port 94 whereby the pressurized gas flows from the sealed container 14, via a quick connect-disconnect tubing conduit 106, to and through the control valve 80 (via inlet orifice 84 and conduit 86) to the selector valve 72, via conduit 96, and therethrough to either the low pressure transducer 46, via conduit 74, or to the high pressure transducer 48, via conduit 76, depending on the position of the selector knob 78. And the third flow position, being referred to as the "bleed" position, connects the inlet port 82 to the third outlet port 98, whereby the pressurized gas flows from the sealed container 14, via a quick connect-disconnect tubing conduit 106, to and through the control valve 80 (via inlet orifice 84 and conduit 86), and through conduit 102 to the bleed discharge orifice 100 for venting the gas to the atmosphere.

Figure 2:
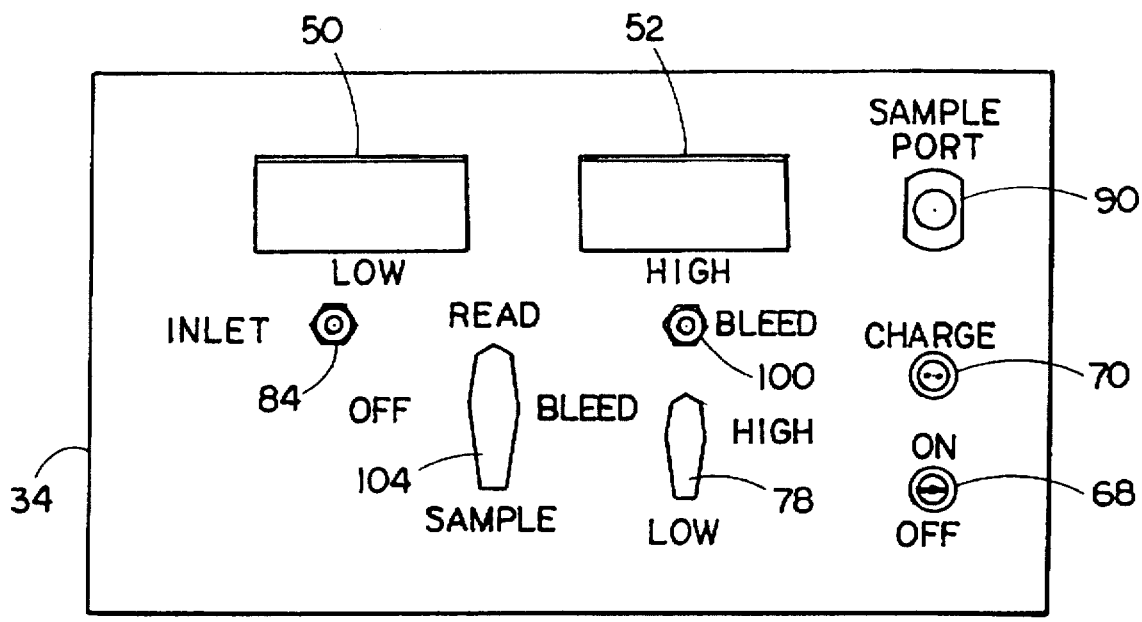
FIG. 2 is a top plan view of the mounting plate, removed from the protective casing, showing the knobs for operating the valves, the visual display units and the different ports as well as the switch and charging connector.
Figure 3:
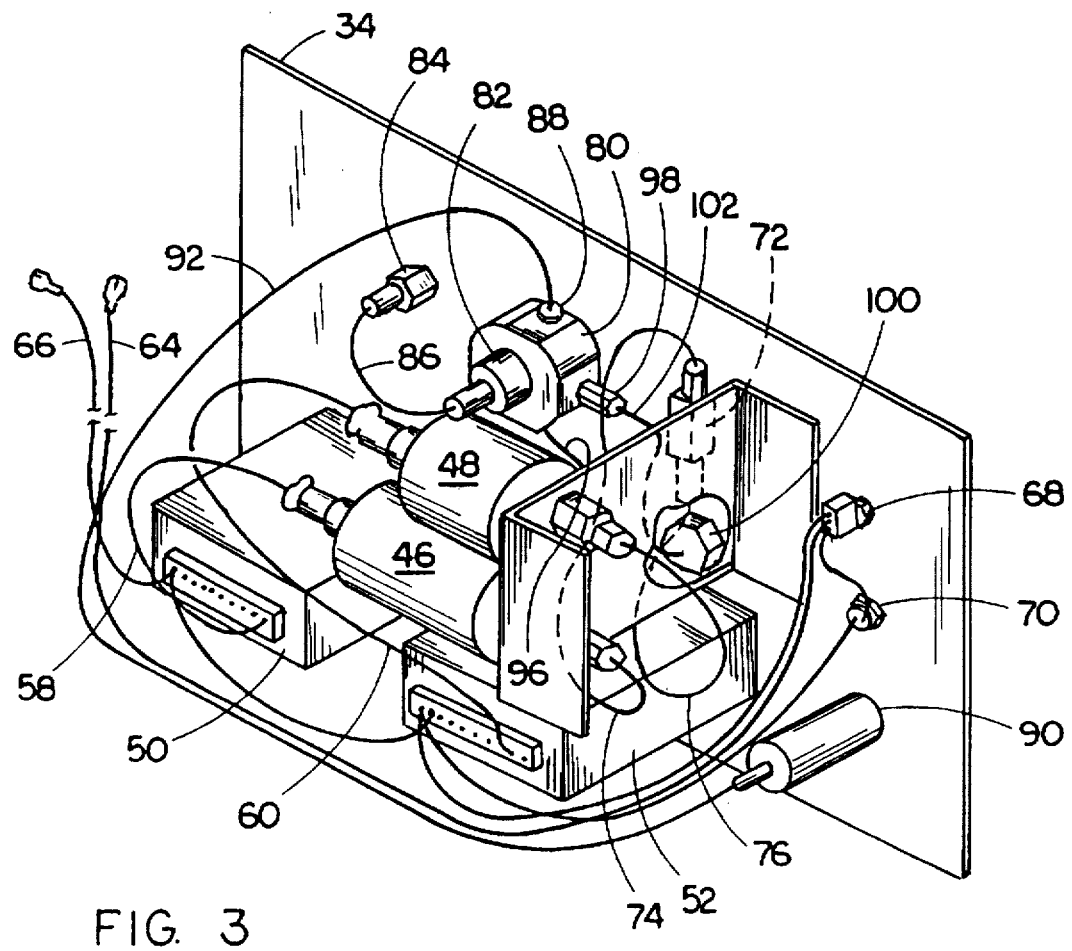
FIG. 3 is a perspective view of the underside of the mounting plate, seen in FIG. 2, showing the various components of the tester.

As best seen in FIGS. 1–3, and especially FIG. 3, the above described components of the tester 10 are attached to the undersurface of the mounting plate 34 and are basically positioned between the mounting plate 34 and the bottom-wall 24 of the box-like base 18 of the protective casing 16, except for the battery 62 which rests on and firmly glued to the bottom-wall 24, and except for the functional control items and view displays, as best seen in FIG. 2, which are mounted on the top surface of the mounting plate 34 for easy and convenient access by an operator. More particularly, each of the low and high range digital display units 50, 52 are mounted in an opening defined in the mounting plate 34 and disposed such that only a visual viewing area of each display unit can be viewed by an operator looking down on the outer top surface of the mounting plate 34 while the remainder of each display unit, along with its associated electrical wiring, is disposed below the inner bottom surface of the mounting plate 34 and above the bottom wall 24 of the box-like base 18. In like fashion, with the selector valve 72 and the control valve 80 being mounted to the under surface of the mounting plate 34, their respective valve stems 73, 81 (seen only in FIG. 1) extend upwardly through openings provided in the mounting plate 34 so that the selector knob 78 and the control knob 104 are positioned above the top surface of the mounting plate 34. Also mounted on the top surface of the mounting plate 34 are the on-off switch 68, the recharging connector 70, the sample port orifice 90, the bleed discharge orifice 100, and the inlet port orifice 84.

OPERATION OF THE TESTER

After a sample of rock (such as a coal sample) is retrieved from a borehole or a lump sample is retrieved from a sampling location, the sample 12 is placed into the container 14 and sealed, making the container airtight. The operator records the time, barometric pressure and ambient temperature to begin the monitoring interval and turns on the tester 10 by moving the power switch 68 to the on position to supply electric power to and thus energization of the low and high pressure transducers 46, 48 and the low and high digital display units 50, 52. With the control knob 104 of control valve 80 being in the non-flow "off" position, the operator then interconnects the sealed container 14 to the tester 10 via a flexible tubing 106 with quick connect-disconnect couplings on each end to the inlet port orifice 88 of control valve 80 and the inlet valve of the top of the container. From experience, the operator estimates whether the sample has either a "low" or "high" gas content and accordingly moves the selector knob 78 of selector valve 72 to either the low flow path position wherein the flow passage is opened to the low pressure transducer 46 or to the high flow path position wherein the flow passage is opened to the high pressure transducer 48. The operator then turns the control knob 104 from its "off" position to the "read" position which opens the flow path for the pressurized gas from the inlet port 82 to either the first or second flow paths 74, 76 respectively to the low pressure or high pressure transducer 46, 48. In response to gas pressure, the pressure transducer 46 or 48 sends a signal, via lead 58 or 60, to the corresponding display unit 50 or 52 which displays the pressure of the container atmosphere on the appropriate digital display which is recorded by the operator. The operator then takes a 20 milliliter vacutainer bottle (not shown) having a slightly negative pressure and a self-sealing stopper and appropriately labels it for a gas sample to be taken. The control knob 104 is now turned from its "read" position to its "sample" position which opens the inlet port 82 to the sample port orifice 90. After allowing gas to flow for about 1 to 2 seconds to purge the sample lines, the vacutainer bottle (not shown) is pressed onto the needle housed within the sample port orifice 90 to retrieve a gas sample for chemical analysis. After the sample is retrieved, the control knob 104 is turned back to the "read" position and either the low range or high range display unit will indicate a small pressure drop from the retrieval of the gas sample. The control knob 104 is now turned back to the "read" position so that the operator determines if pressure needs to be bled further or if the final pressure can be recorded for the sealed container 14. If necessary, the control knob 104 is turned to "bleed" position which opens the inlet port 82 to vent the gas from the container 14 to the atmosphere. Bleeding is complete when the container differential pressure is on the order of a few tenths of a psi over ambient atmospheric pressure. Bleeding the gas in the container is done to avoid gas pressure buildups so that opportunity for gas release from the sample is relatively constant over the monitoring period. The control knob 104 is now turned back to the "read" position so that a final pressure can be recorded for the container 14. Following a day of gas content testing, the battery 62 of the tester 10 can be recharged through a standard 110 volt outlet using a commercially available battery charger attached to the charger connector 70.

It is thought that the present invention and many of its attendant advantages will be understood from the foregoing description and it will be apparent that various changes may be made in the form, construction and arrangement of the parts of the invention described herein without departing from the spirit and scope of the invention or sacrificing all of its material advantages, the form hereinbefore described being merely a preferred or exemplary embodiment thereof.

We claim:

1. A portable tester for reading and displaying the pressure of a gas released from a core sample stored within a sealed container and for taking a sample of the released pressurized gas for chemical analysis thereof for subsequent use in a modified direct method test which determines the volume of gas and specific type of gas contained within said core sample, said tester consisting of:

(a) a low range electrical pressure transducer for detecting a gas pressure within a first range and for producing an electrical signal related to the detected pressure;

(b) a high range electrical pressure transducer for detecting a gas pressure within a second range and for producing an electrical signal related to the detected pressure, said second range of gas pressure being greater than said first range of gas pressure;

(c) a low range display unit electrically connected to said low range electrical pressure transducer for receiving the electrical signal produced therefrom and visually displaying the pressure of said detected gas;

(d) a high range display unit electrically connected to said high range electrical pressure transducer for receiving the electrical signal produced therefrom and visually displaying the pressure of said detected gas;

(e) a selector valve means in flow communication with said low range and high range pressure transducers and having a first flow path to said low range pressure transducer and a second flow path to said high range pressure transducer and a selector knob for selecting gas flow to one of said first and second flow paths;

(f) a control valve means having an inlet port for flow communication to said sealed container, a first outlet port for flow communication to a sample gas canister, a second outlet port in flow communication with said selector valve means for reading the pressure of the flow of gas from said sealed container to said first and second flow paths of said respective low range and high range pressure transducers, a third outlet port for venting to the atmosphere gas contained within said sealed container, and a control knob for selecting the flow of gas from said inlet port to one of said first and second outlet ports;

(g) a battery electrically interconnecting said low range and high range pressure transducers with said respective low range and high range display units; and (h) a portable protective casing for housing said low range and high range pressure transducers, said low range and high range display units, said valve means, and said battery, said protective casing including a box-like hollow base with a hinged enclosure cover and a mounting plate extending over said box-like base and enclosed by said hinged cover, said control knob being mounted on an outer surface of said mounting plate toward said cover and said detector means, said display unit means, and said valve means being mounted on an inner surface of said mounting plate toward a bottom wall of said box-like base.

2. The portable tester as recited in claim 1, wherein said first range of gas pressure being detected by said low range pressure transducer is between 0–25 pounds per square inch absolute and said second range of gas pressure being detected by said high range pressure transducer is between 0–200 pounds per square inch gauge.

3. The portable tester as recited in claim 1, wherein said low range and high range display units are digital display units operable to display said detected gas pressure in digital numeric units.

4. The portable tester as recited in claim 1, further consisting of an on-off switch mounted on said mounting plate of said protective casing and electrically interconnected between said battery power source and said low and high range display units, said switch being movable between an on position for supplying electrical power from said battery to said display units and said pressure transducers therewith for operation thereof and an off position wherein no electrical power is supplied to said display units and said pressure transducers for in-operation thereof.

5. The portable tester as recited in claim 1, further consisting of a charging receptacle mounted on said mounting plate of said protective casing and electrically interconnected to said battery for electrically recharging said battery by an external power source when said battery has a low power charge.

6. The portable tester as recited in claim 1, wherein:

each of said low and high range display units are mounted in an opening defined in said mounting plate and disposed such that only a visual viewing area of said each display unit can be viewed by an operator looking down on an outer top surface of said mounting plate while the remainder of said each display unit along with its associated electrical wiring is disposed below an inner bottom surface of said mounting plate and above a bottom wall of said box-like base;

each of said low and high range pressure transducers are mounted to said inner bottom surface of said mounting plate and disposed above said bottom wall of said base;

said battery power source resting on the bottom wall of said base and disposed below said mounting plate; and each of said selector valve means and said control valve means are mounted on said inner bottom surface of said mounting plate and have a corresponding valve stem extending through said mounting plate for attachment above said outer top surface of said mounting plate to said respective selector and control knobs for access by an operator when said hinged cover of said protective casing is in an open position.

* * * * *